United States Patent [19]
Stapleton et al.

[11] Patent Number: 5,281,516
[45] Date of Patent: Jan. 25, 1994

[54] TEMPERATURE CONTROL APPARATUS AND METHOD

[75] Inventors: Marilyn J. Stapleton, Durham; Warren R. Jewett, Cary, both of N.C.

[73] Assignee: Gene Tec Corporation, Durham, N.C.

[21] Appl. No.: 855,318

[22] Filed: Mar. 23, 1992

Related U.S. Application Data

[63] Continuation-in-part of Ser. No. 227,348, Aug. 2, 1988, abandoned, and a continuation-in-part of Ser. No. 438,592, Nov. 17, 1989, Pat. No. 5,188,963, and a continuation-in-part of Ser. No. 6,768, Nov. 16, 1990.

[51] Int. Cl.$^5$ .............. C12Q 3/00; C12M 1/02; C12M 1/38; F28F 5/00
[52] U.S. Cl. ............... 435/3; 435/287; 435/290; 435/316; 435/809; 165/61; 165/86
[58] Field of Search ............ 435/3, 287, 290, 291, 435/316, 809; 165/61, 86; 219/200, 201, 443

[56] References Cited

U.S. PATENT DOCUMENTS

| | | | |
|---|---|---|---|
| 3,556,731 | 1/1971 | Martin | 435/809 |
| 4,384,193 | 5/1983 | Kledzik et al. | 435/809 |
| 4,609,037 | 9/1986 | Wheeler et al. | 165/86 |
| 4,865,986 | 9/1989 | Coy et al. | 435/290 |
| 4,950,608 | 8/1990 | Kishimoto | 435/290 |
| 5,038,852 | 8/1991 | Johnson et al. | 165/12 |
| 5,061,630 | 10/1991 | Knopf et al. | 435/290 |

Primary Examiner—James C. Housel
Assistant Examiner—T. A. Trembley
Attorney, Agent, or Firm—Olive & Olive

[57] ABSTRACT

An apparatus and method for performing automated sample preparation, DNA amplification and detection, which apparatus has heat-sinking, flat carriers for holding specimens and reagents, devices for heating and cooling and maintaining the specimen to or at any given temperature for any given time periods, and a computer to generate signals that control said temperatures and times.

11 Claims, 6 Drawing Sheets

TEMPERATURE CONTROL APPARATUS AND METHOD

This application is a continuation-in-part of copending U.S. application Ser. No. 07/227,348 filed Aug. 2, 1988, now abandoned, copending U.S. patent application Ser. No. 07/438,592 filed Nov. 17, 1989, now U.S. Pat. No. 5,188,963, and copending U.S. patent application Ser. No. 07/836,348 filed Mar. 3, 1992 and copending international application PCT/US90/06768 (01/006768) filed Nov. 16, 1990, the disclosures of all of which are incorporated herein by reference.

BACKGROUND OF THE INVENTION

The present invention relates to the field of automated analyzers for nucleic acid diagnostics, in particular to temperature control devices. It is well known in the field of molecular biology that a reaction is influenced by the temperature at which the reaction is performed. If the temperature of the reaction varies, the results could be inconsistent with previous assays or with results of the calibration reactions. Precise temperature control to provide heating and cooling cycles is useful in many processes and particularly useful in gene amplification and detection processes.

This invention more fully describes an embodiment of the carrier which incorporates a standard microscope slide as part of the carrier as described in U.S. Pat. No. 5,188,963 and copending U.S. patent application Ser. No. 836,348; and PCT US/90/06768. This invention describes a carrier assembly of multiple carriers which uses a slide as the main portion of each carrier bottom and frames the edges which fit around the slide in keeping with the original carrier format. This invention describes the automated apparatus's temperature control system and its integration with the carrier for more precise temperature regulation.

The in situ amplification process (described in U.S. Pat. No. 5,188,963, and copending U.S. patent applications, Ser. No. 227,348; Ser. No. 836,348; and PCT/90/06768) uses enzymes such as polymerase or ligase, separately or in combination, to repeatedly generate more copies of a target nucleic acid sequence by primer extensions to incorporate new nucleotides or by ligations of adjacent complementary oligonucleotides, wherein each template generates more copies and the copies may themselves become templates. By melting complementary strands of nucleic acids, the original strand and each new strand synthesized are potential templates for repeated primer annealing or ligation reactions to make and expand the number of specific, amplified products. A thermostable polymerase with reverse transcriptase activity and a thermostable ligase are now both available and increase the choice of enzymes and combination of reactions for in situ applications. As stated in copending U.S. patent application Ser. No. 227,348, if RNA in the specimen is the target to be amplified, the specimen is treated with reverse transcriptase to make a nucleic acid complement of the RNA just prior to amplification. Using a thermostable reverse transcriptase polymerase such as rTth (Perkin Elmer, Norwalk, Conn.), it may not be necessary to add another polymerase for rounds of primer extension amplification. The amplification can either be primer extensions in one direction for linear amplification, or in opposing directions, for geometric amplification. The label can either be incorporated as labeled nucleotides or labeled primers for one-step detection or labeled probes may be added in a step following amplification whereby the probes hybridize to the amplified products for detection.

Nucleic acid amplification had been limited to solution reactions wherein the nucleic acid is released from cells or tissue. In U.S. Pat. No. 5,188,963 and copending U.S. patent application Ser. Nos. 227,348 and 836,348, a process to amplify nucleic acid targets within cells was described and a method for embedding the cellular specimens in a matrix was described to immobilize and stabilize the cells during amplification and detection. A number of examples for using in situ amplification are given in U.S. Pat..No. 5,188,963. A photomicrograph of cells which had amplified and labeled DNA was included in Ser. No. 836,348 to show that the amplified fragments are retained in individual cells and such cells can be enumerated under microscopic observation.

The process requires at least one denaturing or high temperature stage, and one primer annealing or low temperature stage in each cycle. To achieve the desired results, the embedded cell specimens are heated to nucleic acid denaturation temperature and temperature control commences before reagent addition. Since the specificity of nucleic acid hybridization is influenced by temperature, uniform and accurate temperature for all specimens is maintained throughout the reaction. The time required for the specimen to be brought to the reaction temperatures can be a large percentage of the time allowed for the biochemical processes to be performed; therefore, means to cycle temperature rapidly and reliably are desirable.

There are various techniques and devices for adjusting temperature of reagents and specimens thereafter controlling the reaction temperature. For example, it is known to use individual reaction heating coils around individual reaction vessels. While a circulating air or water bath can control temperature of a large number of reactions simultaneously, the rate at which heat transfers from such a bath to a reaction vessel is substantially proportional to the difference between the temperature of the vessel and the temperature of the bath, to the heat capacity of the fluid, and to the efficiency of the contact therebetween. (See, for example, U.S. Pat. No. 5,038,852 where circulating fluid reservoirs or Peltier heat pumps are described for heating and cooling a reaction mix.) The specific heat of air is so small that it becomes very difficult to control the temperature of reaction vessels accurately in circulating air. While water has a superior specific heat compared to air, it must be moved rapidly about the reaction vessels to maintain narrow temperature tolerances and, unfavorably, the water supports microbial growth. In addition to fluid baths, it is also commonly known to install reaction vessels in thermal contact with a temperature controlled body or mass having good thermal conductivity and a specific heat as high as practical. For example, a plurality of reaction vessels may be located within an aluminum or copper body.

The aforementioned in situ amplification for cellular analyses, which requires precise temperature regulation, creates a need for an improved apparatus which adjusts and controls the temperature of the cellular specimens An apparatus designed for rapid temperature cycling necessitates reducing thermal loads to increase the rate at which heat transfers occur. The carriers used in this invention are thin, flat reaction vessels whose bottom piece transfers and spreads the heat quickly to the ultra-thin specimen within. Using the word "thin" herein for carrier means that the carrier bottom that conducts heat to the specimen is preferably not thicker than 1 millimeter. Using the word "ultra-thin" herein for specimen means that a rehydrated matrix and specimen is preferably not thicker than 0.5 millimeter. Because the specimen is ultra-thin and represents a significantly greater surface area to volume ratio than what would be found in a conical tube, the specimen temperature more closely matches the temperature of the bottom piece. For e.g., the surface area-to-volume ratio of 100 microliters in a conical tube is 132:1; whereas, the surface area-to-volume ratio in a flat carrier (with a 2 cm×2 cm matrix and specimen holding area) holding an equivalent 100 microliter sample is 830:1, or more than six times greater. For example, a conical microfuge tube filled to a depth of 1 centimeter at a maximum width of 0.62 centimeters has a surface area of 1.32 $cm^2$ and a volume of 0.1 cubic centimeter (100 microliters). A carrier with a sample 2 cm×2 cm×0.025 cm also has volume of 0.1 cubic centimeter, but has a surface area of 8.3 $cm^2$.

When glass slides are inserted in a carrier assembly as separate carrier bottoms, each glass slide becomes part of the heat flow transfer to and from a specimen. A specimen in the thin, aforementioned configuration has greater surface contact with the slide (carrier bottom), thereby reflecting quicker temperature changes with respect to the flat carrier bottom, than a specimen-containing solution with respect to the aforementioned conical tube. Using glass in the bottom carrier piece, or a material with comparable heat conductivity characteristics, also improves the heat transfer capability of the carrier format over standard microfuge tubes made of polypropylene. A flat configuration of the matrix and specimen holding area on a carrier enables convenient microscopic analysis of molecular targets within the individual cells immobilized throughout the specimen.

Discrimination between binding specificity of different nucleic acid primers and probes to target molecules is affected by temperature. Minor sequence variations in nucleic acid base composition may be detected within individual cells either by labeling newly-incorporated nucleotides from specific oligonucleotides and/or amplifying the target sequence and then hybridizing a labeled probe to the amplification products. These sequence variations may be used in DNA-based diagnostics to identify infectious disease, genetic disease, cancer or identity-testing. Precise temperature control is required to use genetic sequence information most fully and produce exquisitely accurate results.

The object of the invention is to provide an apparatus and method of accurately controlling the temperature of simultaneous biochemical reactions, bringing all the individual reactions to a desired temperature, holding the reactions to the specified temperature for a period of time, cooling the reactions to a desired temperature, and holding the reactions at the specified temperature for a period of time. Further objects, features and advantages of the invention will become apparent from a consideration of the following description, taken in conjunction with the accompanying drawing figures.

SUMMARY OF THE INVENTION

The present invention overcomes the limitations and drawbacks described above and provides a device for reaction vessels and an apparatus which rapidly brings cellular specimens to a higher or lower predetermined reaction temperature. The apparatus is suitable for cycling and controlling the temperature of a plurality of reaction vessels and can be readily adapted for use in an automated analyzer of DNA diagnostics.

In accordance with the present invention, an apparatus for providing a controlled temperature environment for a plurality of specimens includes an assembly for receiving specimen carriers, a heating plate with means to raise and lower its position relative to the plane of the specimens and means to create a laminar air flow between the specimens and the heating plate to cool the heating plate and specimens rapidly. A heating element in thermal contact with the heating plate heats the heating plate therein to a predetermined reaction temperature. The apparatus also includes sensing means in thermal contact with the heating plate for sensing the temperature of the apparatus and controlling the heater to reach and maintain the specimen at the predetermined temperature.

In one embodiment disclosed herein the apparatus is generally rectangular in shape with specimen carriers in rows and includes a plurality of platforms on the heating plate extending upwardly therefrom, all in thermal contact with the specimen carriers when the heating plate is in the raised position. When the heating plate is lowered, a plenum is coextensive with the space between the specimen carriers and the heating plate, providing a channel for a laminar air flow to quickly cool the specimens and heating plate. It is understood that other embodiments are equally feasible such that, for example, the specimens could be arranged annularly in an apparatus having an annular heating plate and carrier assembly. In yet another embodiment the heating plate and the carrier assembly may be arranged more vertically than horizontally so that a closed position and an open position (for the distance between the heating plate and carrier assembly) is more descriptive than a raised position or a lower position for either the heating plate or the carrier assembly. While the heating plate moves in the embodiment described herein and in FIGS. 1-6, it is equally possible that the heating plate is fixed and the carrier assembly moves either to contact the heating plate or create a space for the laminar air flow.

The preferred specimen carriers are thin and flat wherein the biochemical reactions are performed in a thin aqueous film or matrix rather than in standard tube or cuvette-type containers. The preferred specimen carrier and the fluid delivery system are further described in U.S. Pat. No. 5,188,963. The thin, flat specimen carriers are best suited for in situ DNA amplifications and detections which integrate specimen collection, preparation and gene detection in one reaction vessel. In the instances where the specimen to be analyzed is put on a standard glass slide for the convenience of microscopic observation, a carrier assembly holding the slides supplies carrier edges and top pieces, and said carrier assembly incorporates other features of a supporting carrier rack such as providing the collecting trough. The glass slide is inserted in the carrier assembly which is then placed in the apparatus for processing just as carriers are positioned in racks described in U.S. Pat. No. 5,188,963.

To accomplish precise heating and cooling, the present invention utilizes a specimen carrier assembly with openings through which a surface of each specimen carrier is in communication with a heating plate. Heating elements, sandwiched within or beneath the heating plate, heat the heating plate and transfer heat quickly and uniformly to the specimen carriers. Means to move the heating plate away from the specimen carriers break communication between the specimen carriers and the heating plate, and cooling commences immediately. A fan directs a laminar air flow in a channel between the surface of the heating plate facing the carrier and the surface of the specimen carrier facing the heating plate. The laminar air flow serves as a medium for the transfer of heat away from both the heating plate and the specimen carriers for rapid and uniform cooling.

The laminar flow cooling system of the invention cools thin, flat specimen containers. Said containers could resemble thin-walled cuvettes or tubes having a thin specimen holding area. The difference which defines laminar cooling is that air between the specimen holders and the heat source is compressed into a rapidly moving stream to cool objects on both sides of the air flow quickly and representative temperatures of both the heating plate and the specimen containers are monitored and adjustments are made in the air flow rate to bring each toward the temperature of the other. The apparatus of this invention provides for control of the temperature of specimens in the carrier and control of the distance between the heating plate and the carrier and control of the laminar air flow cooling. The slides' matrix and specimen holding areas are aligned with the raised heating platforms. The distance between each slide and the corresponding heating platform is uniformly adjusted and may be changed during heating and cooling. Other specimen containers having a thin specimen holding area and made of thin pieces to transfer heat efficiently and which use a laminar air stream for rapid cooling, as described herein, are within the scope of this invention.

Other aspects and features of the invention will be more fully apparent from the following disclosure and appended claims.

DETAILED DESCRIPTION OF THE INVENTION AND PREFERRED EMBODIMENTS THEREOF

Figure 1:
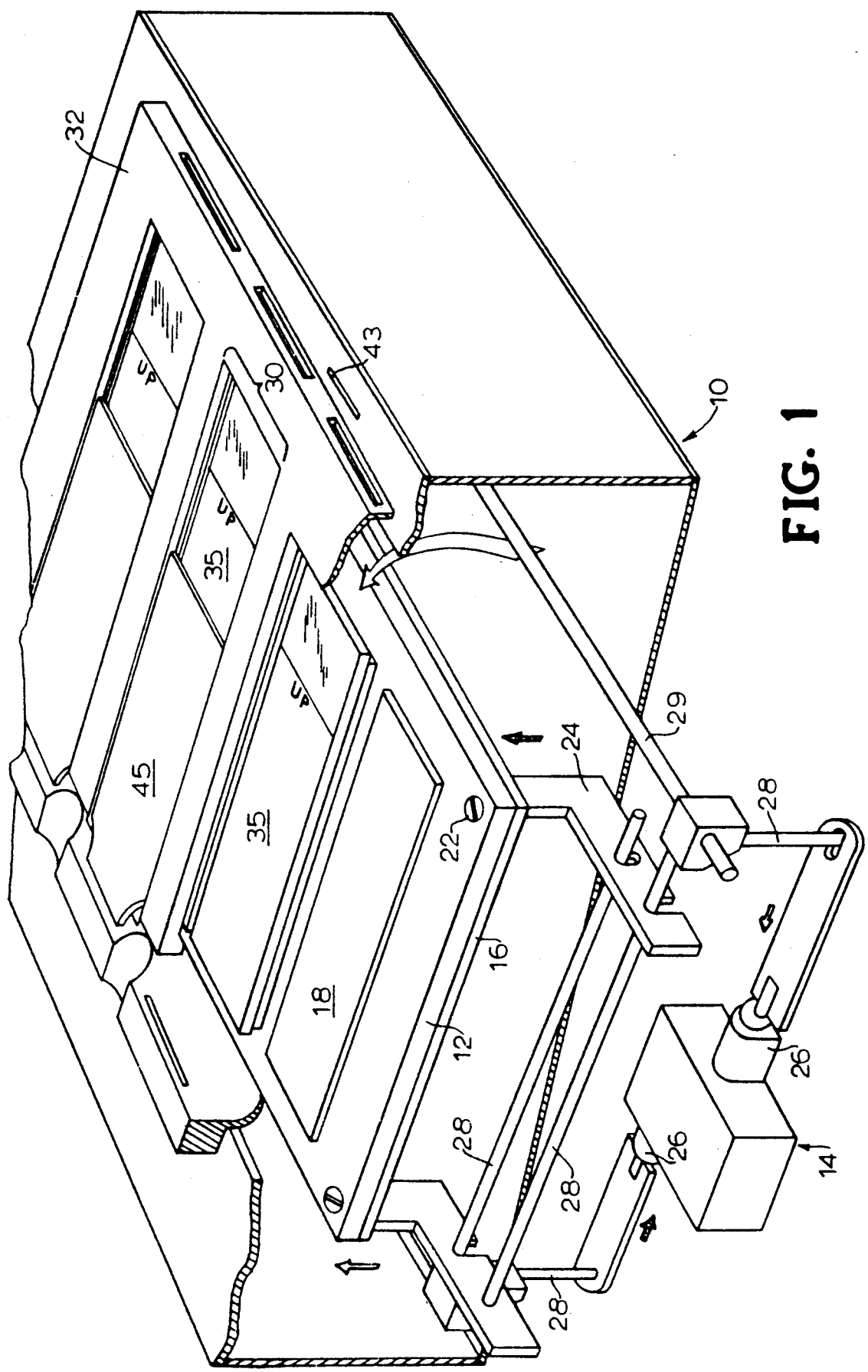
FIG. 1 is a perspective view of the apparatus of the invention showing one embodiment of a heating plate and lifting mechanism and a cut away view of a carrier assembly holding standard microscope slides. Slides are positioned in four carriers showing how said slides contact the heating plate. Two of the carrier top pieces, or covers, are shown in a closed position.

The invention broadly comprises an apparatus for heating and cooling multiple specimens within carriers in a carrier assembly. The specimen holding areas of the carriers are thin so as to spread the specimen for cellular analysis and allow for rapid temperature change. Individual specimen carriers are held in a carrier assembly for molecular processing at precise temperatures. With reference to FIG. 1, a temperature control apparatus 10 in accordance with the present invention includes a heating plate 12, a lifting mechanism 14 and heating element 16. The heating plate 12 is preferably formed of a heat conductive material such as aluminum alloy or copper. Heating plate designs were referred to in co-pending U.S. patent application Ser. No. 836,348. The heating plate surfaces closest to the carrier assembly may have protruding sections in a pattern that permits intimate contact with the carrier bottoms and specific means of heating, such as insulated resistive heating wire elements, may be incorporated in specific locations in the carrier assembly or disposed within the heating plate 12 by milling cavities in the heating plate 12 to direct heat to specific areas of the carrier bottom. Heating elements are fixed within such cavities by means known in art, for example, laser welding, to enclose the heaters.

The heating plate 12 embodied herein has raised platforms 18 integrally formed with the heating plate 12, for example, by machining or die-cast injection molding, or the platforms may be separately formed and bonded to the heating plate by soldering, brazing or with a suitable heat-conductive epoxy compound. If the platforms 18 are formed separately with separate heating elements positioned with the individual platforms 18, the heating plate 12 may be formed of aluminum, or an aluminum frame with as little thermal mass as possible, and the platforms 18 formed from copper. In all cases the heating plate surface meeting the carrier assembly 32 must be shaped so that intimate contact is achieved overall for optimal distribution of heat to the carrier bottom. In the preferred embodiment disclosed herein, the heating element is an insulated thermofoil material (Minco Products, Inc., Minneapolis, Minn.) having a total resistance in the range of about 6–16 ohms and being adapted to dissipate approximately 12 watts of power per square inch when 24 volts DC is applied thereto.

In the preferred embodiment disclosed herein, the temperature sensors 20A and 20B (FIG. 7) comprise thermistors, or thermocouples, bonded to, or embedded in, the heating plate 12 and a representative carrier, respectively. The temperature sensor 20 may have a nominal resistance of approximately 10,000 ohms at 25°

C. Electrical connections for both the heating elements 16 and temperature sensors 20 are provided by means of feed-throughs.

The heating plate 12 has screws 22 and posts 24 connecting it to the lifting mechanism 14. The posts 24 are preferably made of non heat-conductive material and are attached to the heating plate with non-metal screws 22. The lifting mechanism consists of means to raise and lower the heating plate and may be accomplished by any number of possible assemblies such as a combination of squeeze clamp solenoids and levers, or an electric gear motor and cam action. A further lifting mechanism may comprise a stepper motor, switch and double helix, whereby the heating plate is raised and lowered by moving one centrally-located post up and down. Four arms from the center post to each corner of the heating plate support the heating plate, and movement of the double helix raises and lowers the center post. Spring-like action, executed from below the heating plate by means know in the art such as gaskets between the arms and the heating plate "float" the heating plate so that the heating plate surface is aligned with respect to the carrier assembly when the heating plate is raised.

In the preferred embodiment of the lifting mechanism disclosed herein, four tubular solenoids 26 move four lever 28 arms at the same time to lift the four corners of the heating plate 12 and position its top surface with raised platforms 18 in immediate contact with the carriers 30. Referring to FIG. 1, two pairs of arrows show the direction each squeeze clamp moves in order to lift the opposite corner of the heating plate. One of the open arrows shows the direction one solenoid clamp 26 retracts to lift the opposite corner of the heating plate in the direction indicated by the other open arrow when lever arms 28 rotate around a pivot rod 29. The stippled pair of arrows demonstrates a similar action for the other solenoid clamp and heating plate corner.

Figure 2:
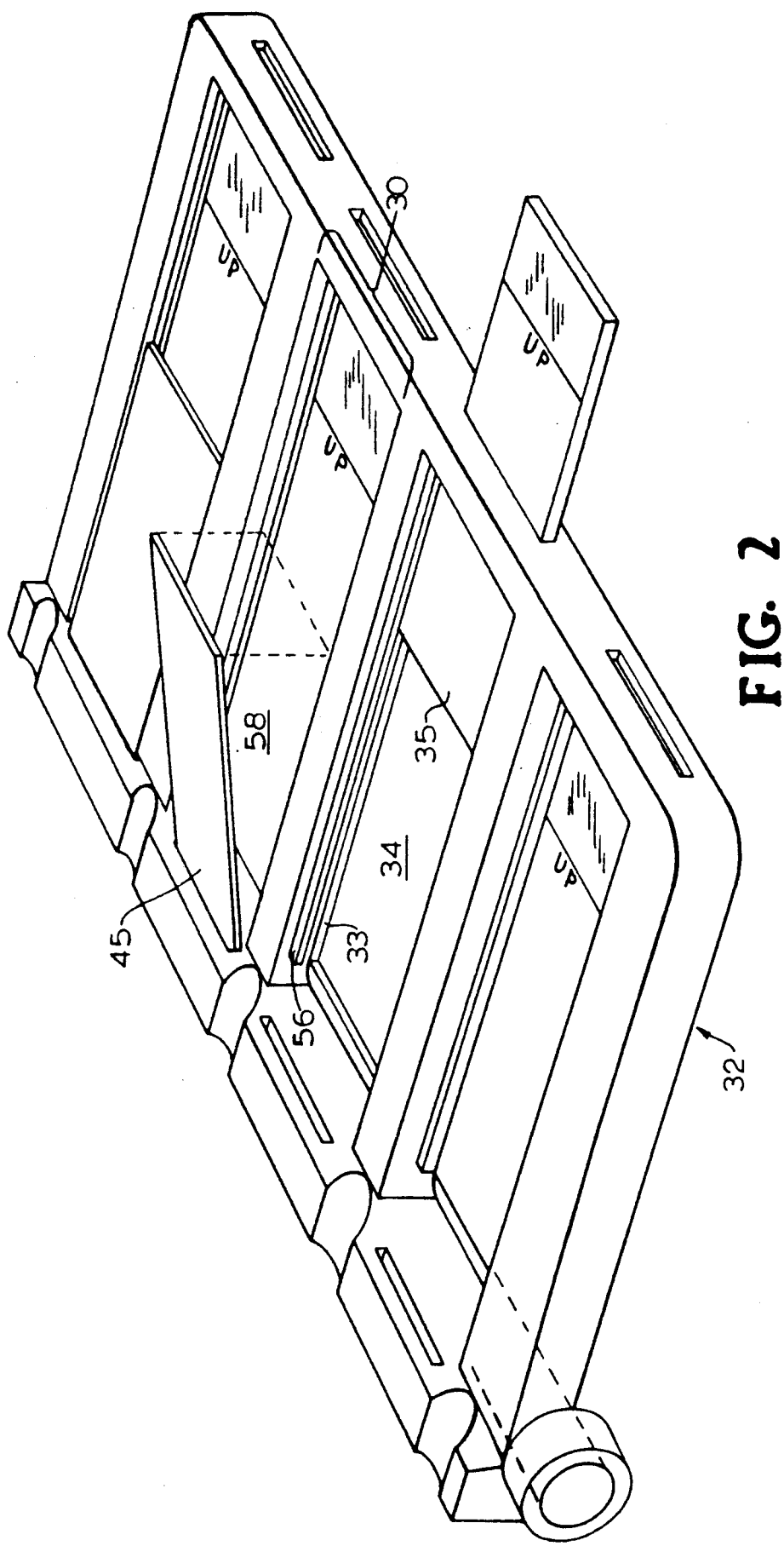
FIG. 2 is an perspective view of a carrier assembly holding glass microscope slides and one slide in a partially inserted position. A dotted line shows one of the covers going from an open to a closed position.

With continued reference to FIGS. 1 and 2, the specimen carriers 30 are held by a carrier assembly 32. The carrier assembly 32 positions the specimen carriers 30 containing the material to be assayed which may be solid or liquid tissue specimens embedded or immobilized in a matrix material on the carrier bottom piece 33. In the embodiment shown the carrier assembly 32 has a plurality of rectangular openings 34 formed therethrough adapted to receive standard microscope slides, each of which said microscope slide 35 becomes part of the carrier bottom 33. The openings 34 are aligned with respect to the platforms 18 on the heating plate 12 so that each specimen carrier bottom 33 makes thermal contact with the respective platform 18 when the heating plate 12 is in the raised position. The preferred specimen carriers 30 are made of glass or a heat-resistant plastic material and are more fully described in copending patent application Ser. No. 438,592.

Referring to FIGS. 3-6, a retainer 38, comprised of ribs 40 and fastened by means of hinges 42 to the apparatus, presses against the carriers 30 between the slide openings when said retainer is closed by a spring-loaded closure 43, insuring thermal contact with the platforms 18 when the heating plate 12 is in the proper position. The retainer ribs 40 define spaces 44 adapted to allow the top piece or cover 45 of the specimen carriers 30 to be opened and closed. The cover actuator 46 grippingly moves over the retainer ribs 40 to open and close the carrier. The spaces 44 also provide a path through the retainer 38 for the delivery of fluid reagents to the specimens as described in U.S. Pat. No. 5,188,963 and copending applications Ser. Nos. 227,348 and 836,348. As is well known in the art, the material to be assayed may comprise a mixture of suitable reagents and a patient specimen or control or calibration sample.

Returning to FIG. 3, a fan 48 connects to a plenum 50 coextensive with the laminar flow air space 52, which occurs when the heating plate 12 is retracted a distance of 2-10 millimeters from the carrier. A baffle (not shown) made as known in the art is configured in such a way within the plenum 50 so as to even out the rate of air flow entering the laminar air flow space at all carrier positions 30. The carrier bottoms 33, and microscope slides 35 which are inserted at carrier positions 30, situated in the carrier assembly 32 form the upper boundary of the laminar flow space 52 and the heating plate forms the lower boundary of the laminar flow space 52.

Figure 4:
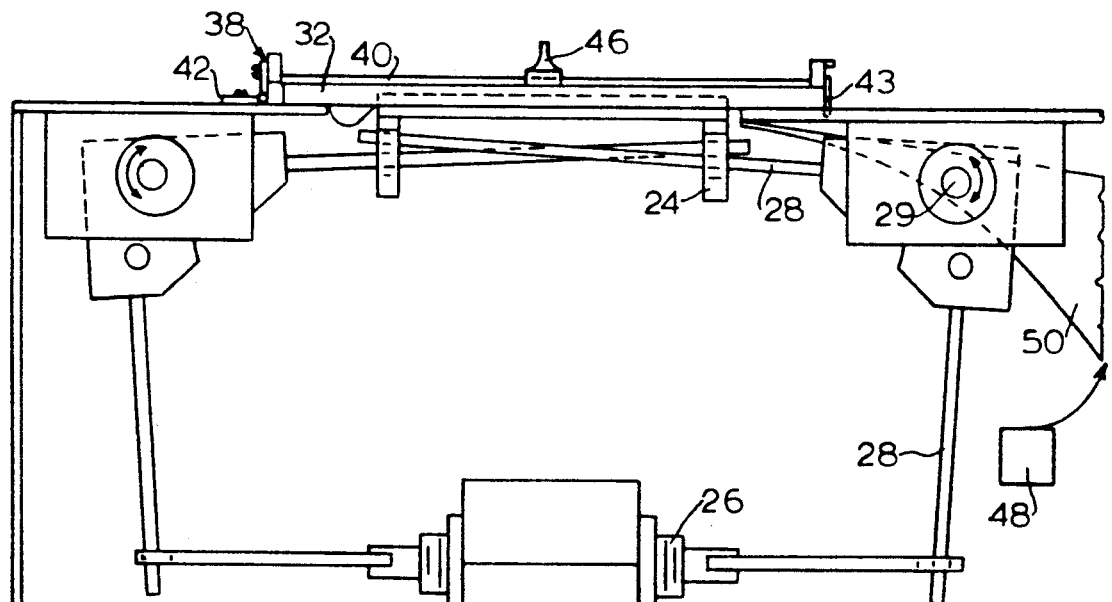
FIG. 4 is an enlarged view showing the path of the laminar air flow between the carrier's slide bottom and the platforms on the heating plate when a minute distance separates the heating plate from the carrier slide bottom.

In FIG. 4 the distance is reduced between the heating plate and carrier to show the heating plate touching the carrier bottom piece. As disclosed in copending application Ser. No. 836,348, included herein by reference, actual temperature data representing the heating plate and the carrier were recorded using a prototype device. The carrier held 25 mm×75 mm glass slides and the distance between said heating plate and slide was constant during cycling. The importance of the data is that heat convected from the heating plate via the air cushion overcame differences in starting temperatures at different cycles to bring the slide closer to the desired higher temperature setpoint, but lower temperature setpoints varied from one cycle to the next. The data suggest that adjusting the distance between the heating plate and the carrier is as least as important, or even more important, in maintaining consistent lower setpoint temperatures versus higher ones. The data also demonstrate that temperature cycling control is possible without intimate contact between the heating plate and the carrier with each in a fixed position, the fixed position affects the slope of the heating/cooling curve, and preferably the distance (which may be 0-2 cm, or somewhere in between at a particular point in the temperature cycling) changes during the programmed temperature cycle.

The instant invention improves temperature regulation by controlling a laminar air flow between the heating plate and the carrier. The invention further provides mechanisms and computer means to control changing the distance between heating plate and carrier. Referring to FIG. 4, the elevational view of one embodiment of a lifting mechanism 14 further shows the positional change of the solenoid-operated 26 lever arms 28 as the lever arms rotate to lift the heating plate 12 at each of the four posts 24. The dotted line shows where the heating plate meets a slide 35 within the carrier assembly 32. Arrows show the direction of rotational movement of the lever arms around the pivot rod 29 to lift the heating plate 12.

Figure 3:
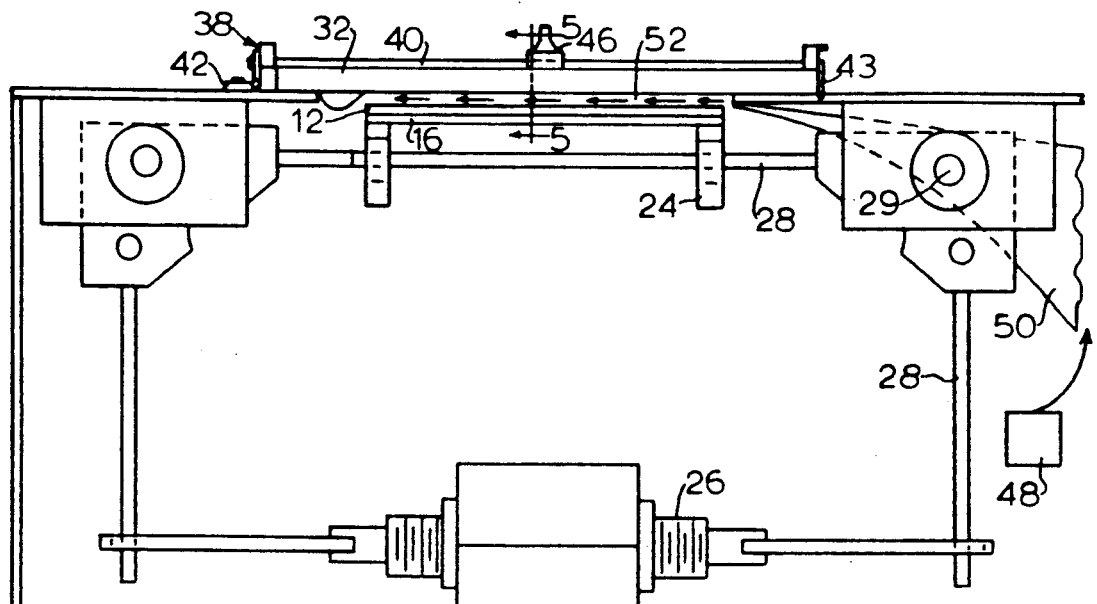
FIG. 3 is an enlarged view showing the path of the laminar air flow between the carrier's slide bottom and the platforms on the heating plate when a measured distance separates the heating plate from the carrier slide bottom.
Figure 5:
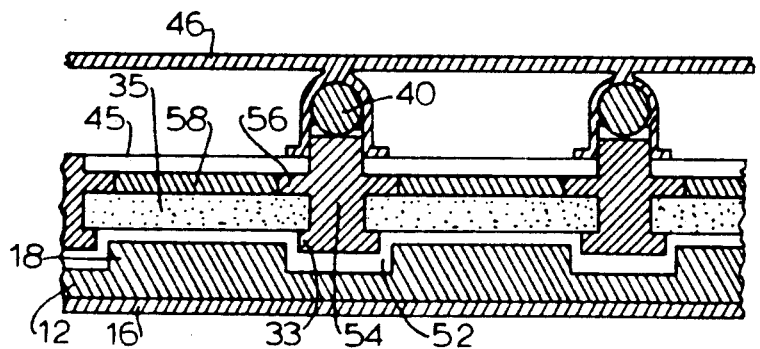
FIG. 5 is a cross-sectional view of a carrier and heating plate taken along line 5—5 in FIG. 3 showing an individual raised heating platform on the heating plate in alignment with a slide positioned in the carrier, carrier edges which define the matrix and specimen holding area between the top (cover) and bottom pieces of the carrier, the bottom carrier edge enveloping the slide and the position of the cover and the retainer.
Figure 6:
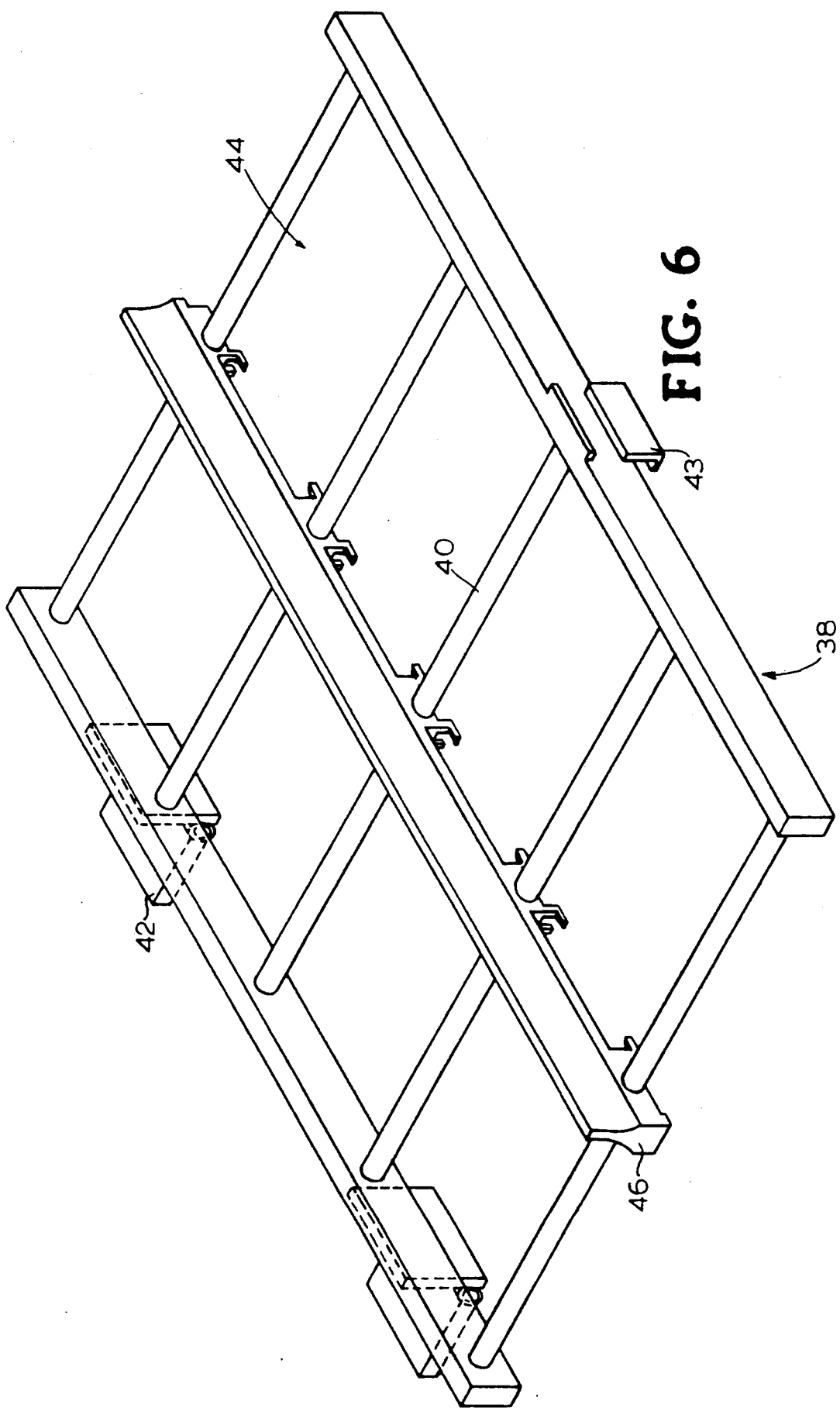
FIG. 6 is a perspective view of a retainer which closes over the carrier, keeping retainer ribs in alignment with the carrier sections between specimens so that carrier edges seal fluids by making contact with the inserted slides. Also shown is the mechanism for opening and closing the carrier top pieces, or covers, over the specimen and matrix holding area.

The cross-section view of the carrier assembly in FIG 5 is located in FIG. 3 by the line marked 5—5. The heating plate 12 is shown in a retracted position relative to the carrier, as in FIG. 3, to illustrate the laminar air flow space 52. The platforms 18 on the heating plate 12 are shown aligned with the slide 35 and carrier bottom 33.

The preferred thickness of the carrier bottom is 1 millimeter or less. The carrier assembly 32 is made of a heat-resistant material and may formed as one plastic piece by compression or injection molding processes to hold slides 35. Alternatively, the carrier may be made by arranging separate sections, which sections are cut from long extruded plastic into appropriate lengths, whose cross-section is shown as extrusion piece 54 in FIG. 5, and which are placed at intervals to accommodates the slides and joined with cross pieces by means known in the art such as laser welding.

The cross-section view in FIG. 5 also illustrates the sequence of parts through the carrier assembly and heating plate starting with retainer ribs 40, the carrier top piece 45, or covers, in a closed position, the position of carrier edges 56 forming matrix and specimen holding spaces 58, the slides 35, carrier bottoms 33, the laminar air flow spaces 52, the heating platforms 18 elevated above the main part of the heating plate 12, the heating plate 12 in a retracted position and the heater 16.

Figure 7:
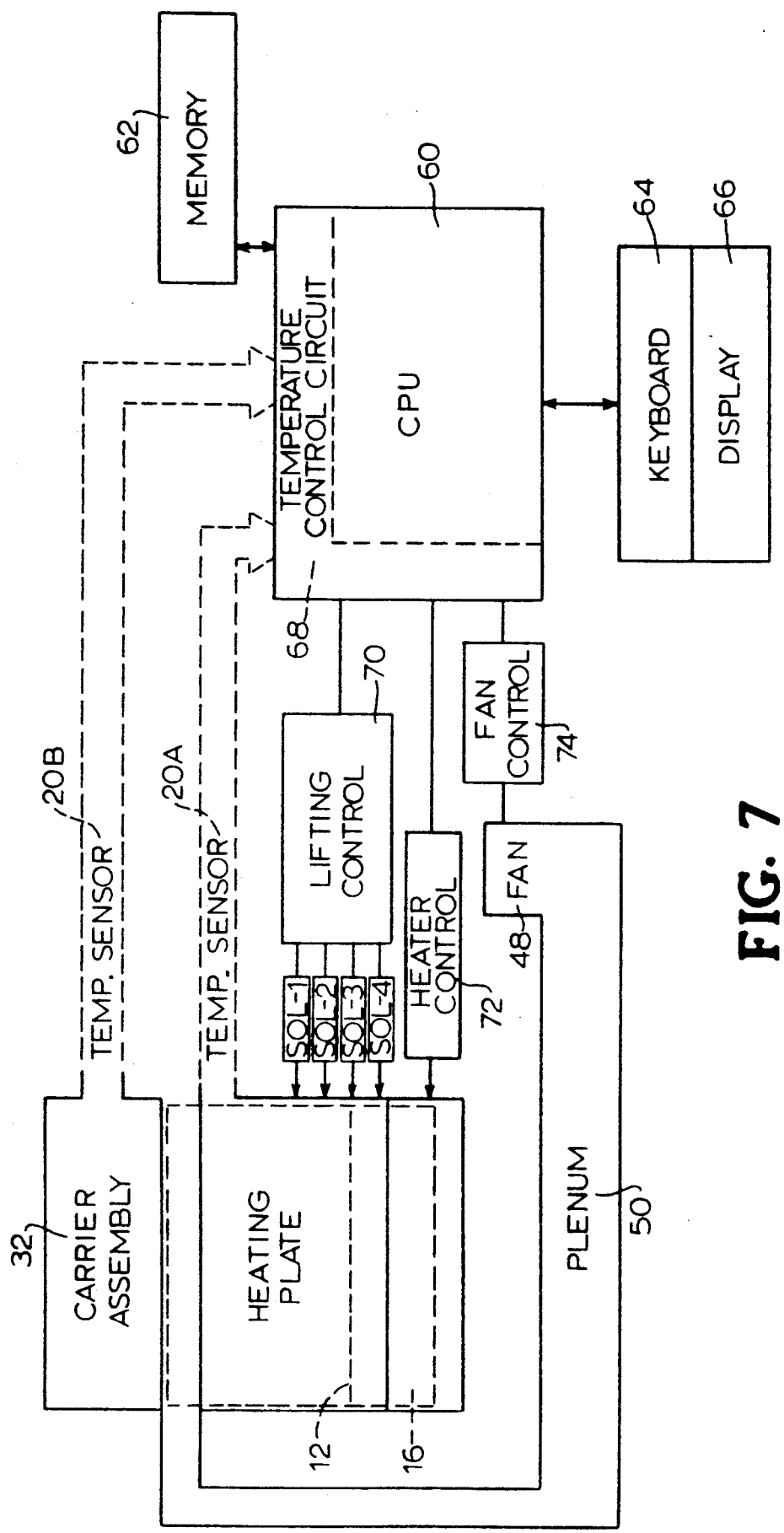
FIG. 7 is a general block diagram of the temperature cycling apparatus.

The apparatus is controlled by a microcomputer or CPU (microprocessor) 60 with memory 62 as shown in FIG. 7. The user enters a heating/cooling profile into the computer via a keyboard 64 or touch pad in response to queries on the menu display 66. A profile comprises a time to heat to setpoint temperature $SP_h$ (ramp), time $T_h$ to reside at setpoint temperature (soak), a selected time to decrease temperature to a lower setpoint temperature $SP_l$ (ramp) and time $T_l$ to reside at lower setpoint temperature (soak). Generally two or three different soak temperatures are selected by the user and default ramp rates are preset, but may be overridden if ramp time is also designated by the user. A temperature, $SP_h$, is preferably within the range of from about 60° C. to 95° C. A temperature, $SP_l$, is preferably within the range of from about 35° C. to 60° C.

The CPU programs comprise instructions to enter and store user profiles and interfaces with a temperature control circuit 68 which contains programming for the lifting control 70, heating control 72 and fan, or laminar air flow, control 74 as diagramed in FIG. 7. The temperature control circuit 68 contains a proportional or a proportional-integral-derivative (PID) algorithm for heating and cooling control. Proportioning may be accomplished either by varying the ratio of "on" time to "off" time, or, preferably with proportional analog outputs as known in the art which decrease the average power being supplied either to the heater or the fan as the temperature approaches setpoint. PID control combines the proportional mode with an automatic reset function (integrating the deviation signal with respect to time) and rate action (summing the integral and deviation signal to shift the proportional band). The 1990/91 Temperature Handbook by Omega Engineering, Inc. (Stamford, Conn.) contains explanations of the various control modes in the "Introduction to Temperature Controllers" on pages P-5 to P-10. Such microprocessor control systems are well known in the art and need not be further described herein. Control functions required for automatic temperature control particular to the apparatus of the invention are more fully explained herein for each step in the logic flow diagram in FIG. 8.

Figure 8:
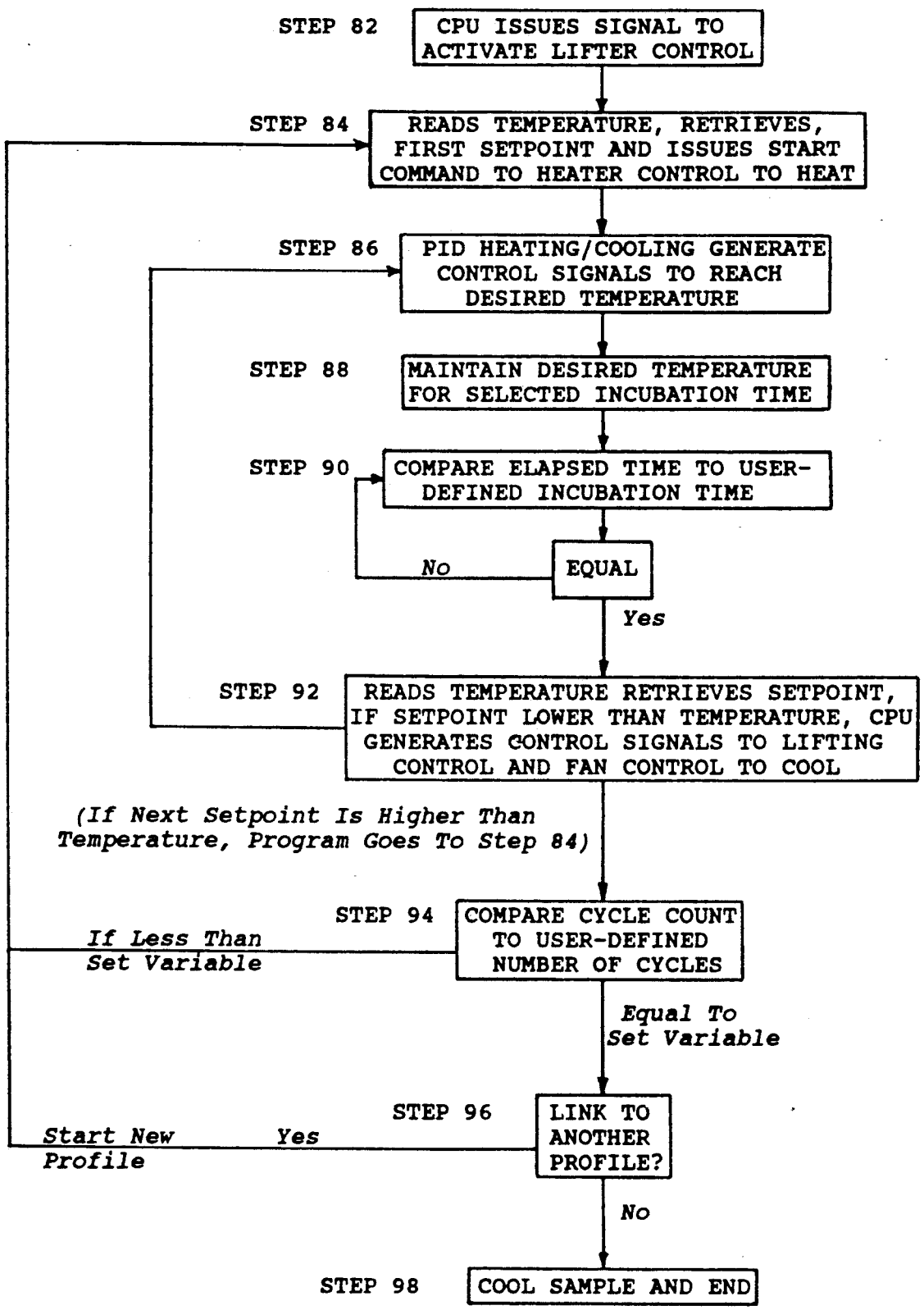
FIG. 8 is a logic flow diagram to show the steps in temperature control.

The process starts with a command to the CPU 60 from the user to begin temperature control in Step 82 of FIG. 8. A user-defined temperature profile is selected from the computer's memory or entered from the keyboard to begin operation. After checking that the retainer closure 43 is in a closed position, the heating plate moves to make physical contact with the slides. The lifting control 70 in this embodiment activates four solenoid-operated lever arms, SOL-1, SOL-2, SOL-3 and SOL-4 in FIG. 7 to position the heating plate in contact with the carrier bottom 33.

The CPU monitors the temperature of the heating plate and, upon receiving the run command, issues the proper command signal to begin heating in Step 84. Upon receiving the proper command, the CPU retrieves the first setpoint data and issues a proper signal to cause heating for a user-defined temperature profile at a default rate and starts the clock. The heater heats the heating plate to the high temperature equal to a user-defined level, which is referred to as temperature variable $SP_h$. The heater begins heating at full voltage and heats to the desired setpoint in the shortest time possible unless the user defines the time period for reaching setpoint temperature. Heat transfers from the heating plate by conduction to the carriers until the desired carrier temperature is reached and during the incubation period to maintain the temperature. The lifting mechanism remains activated until a set point temperature is retrieved that is lower than the previous one.

In Step 86 the CPU reads the temperature of heating plate as the temperature sensor 20-A (FIG. 7) develops a signal as known in the art that is proportional to the temperature of the heating plate 12 and such a signal is converted to a signal for the digital temperature control circuit 68. The CPU monitors the temperature of the heating plate and issues the proper command signal to cause the heater to heat the heating plate until the desired temperature is reached, and then issues the proper commands to the temperature control apparatus to cause the desired temperature to be maintained. Using either the proportional or the proportional-integral-derivative (PID) algorithm, the CPU computes a set point as a target temperature, continuously monitors the temperature of the plate and compares it as it approaches the set point on the user-defined temperature profile. An error signal is generated by comparison of the actual temperature to the calculated set points in the algorithm. The temperature control circuit 68 generates a signal that is proportional to the error voltage applied thereto and the rate of change of such error voltage. The resulting signal from the temperature control circuit 68 generates a modulated output proportional to the signal applied thereto. The output is in turn applied to the heating element 16. The voltage to the heater is controlled by the temperature control circuit and may be turned on and off and the rate of heating may be tuned by adjusting the voltage.

When a specimen carrier slide 35, which has a temperature lower than the selected reaction temperature, is added to the carrier assembly 32, or, when a carrier 30 that is already installed in the carrier assembly 32, is filled or washed with a fluid, e.g. as in U.S. Pat. No. 5,188,963, that is lower than the temperature of the heating plate 12, heat from the heating plate 12 flows to the specimen carrier 30 through the thermally conductive platform 18. In response to the heat flow, localized cooling of the platform 18 in the immediate area of the specimen carrier 30 draws heat from the heating plate 12. As this process continues, the temperature control circuit 68 with the temperature sensor 20-A and the heating element 16 operate as described above to maintain the reaction temperature of the heating plate 12 at the predetermined temperature. Heat flow in the opposite direction occurs if the carrier assembly has a temperature higher than the heating plate, and said heat is absorbed by the larger thermal mass of the heating plate, such that adjustments are made in the heater control.

In Step 88 the CPU keeps track of the elapsed time at particular temperatures to implement desired incubation periods. At least one temperature sensor 20-B (FIG. 7) is placed in a specimen carrier 30 and used to develop a signal. The temperature is monitored via sensor 20-B and the CPU determines whether the carrier is at the correct process temperature. During ramp periods the carrier temperature may lag behind in ramping to a higher setpoint temperature or said carrier temperature may move ahead in ramping to a lower temperature at any given moment in time. For this reason it is important that elapsed time for incubation start when the carrier bottom, not the heating plate, attain soak temperature. The microcomputer control system may start counting the incubation period when temperature sensor 20-B, representing the temperature of the slide 35 or carrier bottoms 33, reaches the predetermined temperature. To implement timing of the incubation period, the computer restarts a clock and times the elapsed time from when the temperature sensor 20-B equals the temperature, $SP_h$. The incubation time variable is generally set by the user according to the requirements of a desired biochemical process.

In Step 90 the CPU compares the elapsed time that the slides are at the desired incubation temperature, $SP_h$, with the selected incubation time, $T_h$. If the actual time is less than the selected time, the program continues to maintain temperature and compare the elapsed time.

When the elapsed time that the slides are at temperature, $SP_h$, equals the desired incubation time as determined in Step 90, the CPU sends the proper command in Step 92 to the heating and cooling apparatus to cause the heating plate to be cooled toward a low temperature, $SP_l$, set by the user.

In some profiles the next setpoint temperature after moving to a higher temperature may be an even higher temperature. In this case the program reenters at Step 84.

Control of laminar flow cooling is integrated into the temperature control circuit 68 as follows. When the next desired temperature of the heating plate 12 is lower than the present heating plate temperature, the temperature control circuit 68 develops a signal to the lifting control 70 to deactivate the solenoids, causing retraction of the heating plate 12. A simultaneous signal to the air flow control 74 activates the fan 48. Air enters the fan 48 and is pressurized into the plenum 50 into a laminar air flow through the laminar flow air space 52. Air flows through the laminar air flow space 52 between the platforms 18 and specimen carrier bottoms 33, removing heat from he specimen carriers 30 and the heating plate 12. The laminar air flow space 52 is thin enough and the air flow pressurized enough by compressing it into a thin space that air turbulence is kept to a minimum.

The program returns to the proportional or PID algorithm in Step 86 to execute heating/cooling control towards a lower setpoint in a similar way in which control was executed towards a higher setpoint, but involving different output control signals. The transmission of commands by the CPU activate a laminar air flow to cool the heating plate and the carriers simultaneously. The temperature of the heating plate 12 and the slide 35 or carrier bottom 33 are monitored by the CPU and an error signal is generated by comparison of the actual temperature to the calculated set points in the proportional or the proportional-integral-derivative algorithm to control the temperature of the heating plate. Periodically, an error signal based upon the comparison between the computed slope of the user-defined temperature profile and that of the new set point is generated from calculation of the slope and the elapsed time. The error signal is converted to the proper control signal to control the lowering of temperature to a lower setpoint.

The speed of the fan is controlled by inputs from temperature sensors 20A (representation of heating plate temperature) and 20B (representation of slide carrier temperature) to the proportional controlling algorithm. Changing the speed of the fan increases or decreases the airflow so that the rate of cooling is within bounds of the user-defined time or the default rate set by the program. The adjustments in airflow compensate for fluctuations in the temperature of intake air and internal heat build-up within the apparatus. When sensor 20-B reaches the lower setpoint temperature, the clock starts counting the elapsed time set for the incubation period, $T_l$. If the error calculated by the CPU between sensor 20-A and sensor 20-B indicates that sensor 20-A is lower than sensor 20-B when the setpoint temperature is reached, the heater is activated; if sensor 20-A is higher than sensor 20-B, the airflow continues to cool the plate after sensor 20-B reaches the low setpoint temperature. Comparing thermal loss rates detected by sensors 20-A and 20-B during the cooling phase and making the aforementioned adjustments work toward equilibrating the temperature of the heating plate and the carrier just as the lower setpoint temperature is reached. At the point when the heating plate and slide carriers are both very near the low setpoint temperature, a control signal activates the lifting mechanism to restore contact between the heating plate and the carrier and another signal to the fan control deactivates the fan. Maintaining a stable temperature for an incubation time period operates similarly for high and low setpoint temperatures. Heat loss to the surrounding environment requires activating the heater control to keep heating plate at low setpoint temperature.

The controller algorithm is also programmed to change fan speed when a differential temperature between sensor 20-A and 20-B is greater than a predetermined amount. Ideally, the heating plate and the carrier are designed to have balanced thermal load and heat loss characteristics. Variable airflow works to fine tune cooling so that when cooling is achieved in less than the user-defined ramp time, or a predetermined default time, or the temperature differential between sensors 20-A and 20-B is greater than a predetermined amount, a decrease in airflow allows more efficient convective transfer of heat from the heating plate through the air cushion to the carrier, or vice versa, and works toward achieving thermal equilibration before low setpoint is reached.

Step 88 following a cooling phase toward a lower setpoint temperature is the same as one that follows moving to a higher setpoint temperature. The CPU measures the elapsed time from the time the slides temperature reaches the $SP_l$ of the heating plate.

Step 90 again compares elapsed time to the user-defined low temperature incubation time, $T_l$. As soon as the elapsed time equals the desired low-temperature incubation time, $T_l$, Step 92 involves the CPU retrieving the next setpoint temperature in the profile and continues until all setpoint temperatures have been executed.

When one profile is complete, the CPU counts the number of times the profile has been run and compares the number to a user-defined variable in memory. The number of times a profile is to be run is the cycle count. In Step 94 the CPU compares the cycle count to the user set variable. If the cycle count does not match the desired number of cycles, processing returns to Step 84. If the cycle count equals the set variable for the desired number of cycles, processing proceeds to Step 96.

After the desired number of cycles has been performed, Step 96 determines whether the user wishes to run another temperature profile stored in another "file" or database. Every temperature profile entered by the user has a link data field in which there is stored the profile identification of the next file or temperature profile to be run, if any. The contents of this field are read. If the field finds a profile number in the link field, then processing returns to Step 84 and restarts by retrieving the first setpoint temperature in the new profile and continues processing through Step 96 again to achieve each setpoint temperature in the profile for the set number of cycles.

In Step 98 the contents of the data link field are read and if the user has made no further entry to the link field, signals to lifter and fan controls work to cool the heating plate until no further reduction in temperature occurs. When the heating plate temperature as sensed by temperature sensor 20-A is not lowered for a preset time period, an "end" message is displayed and the control functions shut off the temperature control apparatus.

Automated DNA analyzers containing the temperature control apparatus may or may not utilize temperature control during other functions. In many instances controlled temperature is desirable to achieve consistent clinical results and the invention herein may be used to replace other temperature control systems for a more precise temperature control. The localized heating provided to each specimen carrier 30 on the apparatus 10 is very rapid and precise, particularly in comparison to other air and water bath techniques.

The unique heating and cooling system combines the conductive heating via the heating plate 12, providing means to distance the heating plate 12 from the specimen carriers 30, and convection cooling via the laminar air flow. A primary difference between the apparatus of the invention and other kinds of moving air systems, which are used to remove heat from the reaction vessels or heat sinks, is that the thermal load of the system has been reduced to a heating plate 12 of just sufficient mass to spread heat evenly and the specimen carriers 30 themselves become part of the heat sinking system. Since the temperature at which heat transfers from the reaction vessel to the laminar air flow is substantially proportional to the difference between the temperature of the vessel and the temperature of the air, cooling the specimen carrier from high temperatures of 95° C. with air at 25° C. or lower is rapid at temperature ranges between 55° C. and 95° C. The heat transfer capacity of the fluid air is increased by increasing its flow rate to supply air of lower temperature to the laminar flow space 52. The efficiency of the contact between the air flow and the surfaces to be cooled is increased by pressurizing the air flow into a thin laminar pathway, thereby, reducing air turbulence.

Studies using glass slides, 1 mm×25 mm×75 mm, as specimen carriers 30 demonstrated in situ DNA amplification as shown in copending patent application U.S. Ser. No. 227, 348. The studies made evident that spacing the specimen carrier a distance as short as 2 mm from the heating plate 12 permitted more rapid cooling of the glass slide and the air cushion in this space further increased the rate of cooling over cooling that could be achieved when the slide was in contact with the heating plate. Temperature data results for heating specimen carriers was included in the specification of copending patent Ser. No. 836,348. The instant invention provides a means for moving air through the air cushion, said air flow directed between the carrier and the heating plate and describing the invention herein comprising a temperature control apparatus for DNA-based detections in cellular diagnostic tests and the essential controlling program logic to attain precise temperature control.

The use of DNA amplification cycling temperatures for annealing and denaturation are both above ambient air temperatures, making refrigeration or Peltier-cooling of the specimen carriers unnecessary in automated clinical DNA analyzers. However, a means of refrigerating or Peltiercooling air may be employed to prechill the air entering the fan and plenum, thereby augmenting the speed of cooling by increasing the temperature differential between the specimens and the air used to cool them.

Other modifications of the above-described embodiments of the invention as used by those of skill in the mechanical and electrical arts and related disciplines are intended to be within the scope of the invention.

The flat, thin configuration of the specimen carrier 30 is a departure from the commonly used centrifuge tube or cuvette. A specimen carrier assembly 32 also has a considerably different configuration than found in support racks or blocks designed for tubes or cuvettes. In tube and cuvette-type vessels the dynamics of the biochemical within the contained solution are subject to molecular distribution in the solution. The flat specimen carrier makes use of a supporting matrix and thin-film fluid dynamics for molecular processing. The flat specimen carrier assemblies 32, adapted to use a standard microscope slide 35 as part of the carrier bottom 33, are caused to press against the microscope slide 35 by the retainer 38 to insure good thermal contact between the slide 35 and the heating plate. Together the heating control 72, fan control 74, and lifting control 70 comprise a temperature control circuit 68 in a CPU to meet the demands of DNA amplification temperature cycling for clinical DNA analyzers.

The preferred way of doing the method is described as follows. The method utilizes standard microscope slides, either blank slides or ones with cellular specimens on them. The slides are inserted into a carrier assembly and the carrier assembly is loaded into the slide temperature control apparatus. A temperature profile to warm the slides to a temperature just above the gelling temperature of the matrix material insures even spreading in the matrix and specimen holding area before gelation. Plain liquid agarose, or liquid agarose mixed with cell suspensions, is added to the slide, filling the matrix and specimen holding area of the slide under the cover. For example, 5 ul of a cell culture solution ($10^6$ cells/ml) may be mixed with 500 ul of 1% agarose (Molecular Biology Grade Agarose, IBI, New Haven, Conn.). Another temperature profile allows the matrix temperature to drop below its gelling temperature, forming a gel matrix embedding the specimen. After gel matrices have formed, slide covers are opened with the actuator on the retainer.

A freshly-prepared specimen treatment solution consisting of 1 mg/ml Pronase (Life Technologies, Rockville, Md.) in 0.01 M Tris.Cl pH 7.8, 0.001 M EDTA, and 0.1% Triton X-100 (v/v) is added to the matrix surface in excess and incubated at 37° C. for 5-15 minutes. If RNA is the molecular target, RNAase inhibitors as known in the art would be included in the treatment solution. The mixture is rinsed from the matrix by three 500 ul washes of dH$_2$O over 15 minutes. The matrices are then dried to the upper surface of the slides by ramping to and maintaining a 85° C. temperature. The in situ sample preparation method unmasks DNA within the matrix-embedded specimen and permits the nucleic acid of the specimen to be used as a template for transcription.

Specimen DNA is denatured by saturating the matrix with 500 ul dH$_2$O and using a temperature profile that heats the carrier to 95° C. and maintains 95° C. for 3-5 min. Adding dH$_2$O drop by drop as needed keeps the matrices from completely drying out during denaturation. The target nucleic acids within the nucleoid of the specimen's cells or within virions are available for primer hybridization and polymerase activity. The genetic material is capable of acting as a template for transcription of DNA or reverse transcription of mRNA within the treated cells using an exogenous polymerase.

A temperature profile heats slides to a primer annealing temperature of, for example, 72° C. and maintains temperature while amplification reagents are added. Each partially-dehydrated matrix is rehydrated with 100 ul of the nucleotide/primer mix, 5 Units of Taq DNA Polymerase (Boehringer Mannheim, Indianapolis, Ind.). In the one-step method at least one of the nucleotides is modified in order to detect incorporation. The nucleotide mixture for example may contain 140 uM each dATP, dGTP and dCTP, 70 uM dTTP and 70 uM Digoxgenin-11-dUTP (Boehringer Mannheim) in buffer (10 mM Tris.Cl, 50 mM KCl, 1.5 mM MgCl$_2$). The primers are specific for the target sequence, for example, cultured cells of CaSki or SiHa which contain integrated copies of human papillomavirus type 16 (HPV-16), are detected by using one or more specific primers at 1 uM each for type-specific regions in the E5, E6 or E7 gene sequences of HPV-16.

A temperature profile for amplification thermal cycling consists of, for example, ramping to and maintaining 72° C. for 2 minutes and ramping to and maintaining 95° C. for 20 seconds for 25 cycles, and ending with a profile of 10 min @ 72° C. Polymerase activity utilizes the target template within the nucleoid of cells each time the previous extension product melts under temperature denaturation and permits another primer molecule to bind and initiate polymerization. Adding a strip of rubber cement at the cover's edge will keep matrix from drying out, or dH$_2$O may be added drop by drop at the cover's edge as needed to replenish volume which may be decreased by evaporation.

After amplification, matrices are rinsed by filling the fluid receiving area with dH$_2$O or detection buffer to start fluid flow through the carrier. The matrices are rinsed by first adding dH$_2$O to one edge of the cover slide, and then 1 ml of TMN (40 MM Tris.Cl, pH 7.8, 6 mM MgCl$_2$, 5 mM NaCl), so that the fluids passed slowly through the diffusion layer between each matrix and its cover. Two ul of anti-Digoxgenin monoclonal antibody from the GENIUS TM Detection System (Boehringer Mannheim) in 225 ul TMN are added to each matrix and incubated for 30 min at 37° C. Two ml of suitable alkaline phosphatase substrate buffer is added slowly for 15 minutes to rinse unbound antibody conjugate away before adding alkaline phosphotase subtrates, NBT (4.4 ul) and BCIP (3.3 ul) in 500 ul of the AP substrate buffer to the matrices. The reaction is incubated with a temperature profile of 1-2 hours at 35° C. and stopped by the addition of 2 ml dH$_2$O through the diffusion layer. The matrices are stained, still within the carrier, for 15 minutes in nuclear fast red to counterstain cellular structures. The carrier assembly is removed from the apparatus and the slides are removed from the carrier assembly and placed on the microscope stage. The cells are observed within the matrices under the microscope and both negative cells without the amplification label and positively-identified cells are visible. The amplified product is observed to remain within the target cells and enable such cells to be enumerated. Cells having copies of the HPV genome integrated into their genome may be identified by this method. The flat matrix format maintains cellular and tissue structures so they may be visible after processing. The use of polymerase activity to amplify in situ increases detection sensitivity, permits unambiguous signal detection and enables the genetic entity to be tied to specific locations in the specimen.

Detection systems utilizing biotin, digoxgenin, fluorescence, antibodies or enzymes or combinations of these produce unambiguous signals within cells embedded in an agarose matrix. If primers or nucleotides are not labeled during amplification, labeled oligonucleotides may be hybridized to amplification products for a 30-minute incubation, followed by rinsing twice at 5 minute intervals and once with slide at stringent temperature without zone spreading of signal from target cells. Standard aqueous hybridization buffers without formamide and standard SSC washes of 500 ul each may be used as known in the art. Labeled cells are visualized with standard light or fluorescent microscopy, depending upon which label is used.

In summary, the present invention provides an apparatus for performing automated sample preparation, DNA amplification and detection, which apparatus has heat-sinking, flat carriers for specimens and reagents, means from heating and cooling and maintaining the specimen to or at any given temperature for a given time period, and a computer means to generate signals that control said temperatures and times.

While the invention has been described in detail with respect to specific illustrative examples and embodiments, it will be apparent that numerous other variations, modifications and embodiments are possible, and accordingly all such variations, modifications and embodiments are to be regarded as being within the scope of the invention. Such variations include, but are not limited to the detection of proteins or other cellular components using known detection methods and reagents.

What is claimed is:

1. An apparatus for providing temperature control to a specimen carrier, comprising:
    (a) one or more specimen carriers, each of said specimen carriers comprising a compartment for holding a specimen and reaction fluids;
    (b) an enclosure having an interior space and having a site for positioning said one or more specimen carriers;

(c) a temperature-controlled plate located in said enclosure, said temperature-controlled plate having a first position in thermal contact with one side of said one or more specimen carriers placed at said site and a second position out of said thermal contact;

(d) means for moving said temperature-controlled plate between said first position and second position;

(e) means for providing laminar air flow between said temperature-controlled plate and said one or more specimen carriers when said temperature-controlled plate is in said second position;

(f) temperature control means capable of adjusting the temperature of said temperature-controlled plate in response to control signals; and (g) computer means connected to said temperature control means and to said means for providing laminar air flow, wherein when said temperature-controlled plate is in the first position, the temperature of the one or more specimen carriers may be brought to a first temperature through thermal contact with the temperature-controlled plate and when the temperature-controlled plate is int he second position, laminar air flow provided between the temperature-controlled plate and the one or more specimen carriers may be used to bring the one or more specimen carriers to a second temperature.

2. An apparatus for providing temperature control to a specimen carrier according to claim 1, wherein the temperature-controlled plate is a heating plate.

3. An apparatus for providing temperature control to a specimen carrier according to claim 1, wherein the means for moving the temperature-controlled plate between the first and second positions comprises means for lifting the temperature-controlled plate into contact with the one or more specimen carriers and for lowering the temperature-controlled plate away from the one or more specimen carriers.

4. An apparatus for providing temperature control to a specimen carrier according to claim 1, wherein said compartment is formed by a carrier bottom and a cover, said cover movable between an open and closed position, and used for holding specimens and for treatment with reaction fluids.

5. An apparatus for providing temperature control to a specimen carrier according to claim 1, wherein the first temperature is a temperature which denatures nucleic acid complexes and the second temperature is chosen to be just below the melting temperature of primer oligonucleotides.

6. An apparatus for providing temperature control to a specimen carrier according to claim 1, further comprising sensing means in thermal contact with the temperature-controlled plate and connected to said computer means, wherein when a selected temperature is detected by said sensing means, said computer means causes the distance between the temperature-controlled plate and said one or more specimen carriers to change.

7. An apparatus for providing temperature control to a specimen carrier according to claim 6, wherein when said selected temperature is detected, laminar air flow between said temperature-controlled plate and said one or more specimen carriers is provided by said means for providing laminar air flow.

8. An apparatus for providing temperature control to a specimen carrier according to claim 1, wherein said means for providing said laminar air flow comprises a fan directing air through a plenum to a smaller space between said temperature-controlled plate and said one or more specimen carriers.

9. An apparatus for providing temperature control to a specimen carrier according to claim 1, wherein said temperature-control means is a part of said computer means.

10. A method for providing temperature control to one or more specimens in one or more specimen carriers in a specimen treatment process, comprising:

(a) placing one or more specimen carriers in an enclosure having an interior space and having a site for positioning one or more specimen carriers, each of the said one or more specimen carriers comprising a compartment for holding a specimen;

(b) providing:
  (i) a temperature-controlled plate located in said enclosure, said temperature-controlled plate having a first position in thermal contact with one side of said one or more specimen carriers placed at said site and a second position out of said thermal contact;
  (ii) means for moving said temperature-controlled plate between said first position and second position;
  (iii) means for providing laminar air flow between said temperature-controlled plate and said one or more specimen carriers when said temperature-controlled plate is in said second position;
  (iv) temperature control means capable of adjusting the temperature of said temperature-controlled plate in response to control signals; and
  (v) computer means connected to said temperature control means and to said means for providing laminar air flow, wherein when said temperature-controlled plate is in the first position, the temperature of the one or more specimen carriers may be warmed through thermal contact the temperature-controlled plate and when the temperature-controlled plate is in the second position, laminar air flow provided between the one or more specimen carriers and the temperature-controlled plate may be used to cool the one or more specimen carriers;

(c) performing temperature-changing steps in a predetermined sequence along with one or more specimen treatment steps said temperature-changing steps including:
  (i) changing the temperature of said one or more specimen carriers to a warmer desired temperature by moving said temperature-controlled plate to said first position utilizing said means for moving said temperature-controlled plate between said first and second positions with respect to said site and providing control signals to adjust the temperature to said warmer desired temperature and to maintain the temperature of the temperature-controlled plate at said warmer desired temperature for a first predetermined time period; and
  (ii) moving said temperature-controlled plate to said second position utilizing said means for moving the said temperature-controlled plate between said first and second positions and one ore more specimen carriers utilizing said means for providing laminar air flow to adjust the temperature of said temperature-controlled plate to a cooler desired temperature; and maintaining said cooler desired temperature for a second predetermined time period.

11. A method of providing temperature control to one or more specimens in one or more specimen carriers in a specimen treatment process according to claim 10, and wherein the sequence of the predetermined sequence of temperature-changing steps and the specimen treatment steps comprises:

(a) warming the one or more specimen carriers to a temperature just above a gelling temperature of a selected matrix material before adding liquid matrix material to the one or more specimen carriers;

(b) after adding liquid matrix material containing a specimen having DNA to said one or more specimen carriers, cooling the one or more specimen carriers to lower than said gelling temperature;

(c) adding a treatment solution to the one or more specimen carriers and adjusting the temperature of the one or more specimen carriers to allow a desired treatment to occur;

(d) heating the one or more specimen carriers to 85° C. and maintaining g the temperature at about 85° C. until the gelled matrix material is dehydrated;

(e) denaturing the specimen DNA by saturating the dehydrated matrix material with distilled water and heating to about 95° C. for about 3-5 minutes;

(f) heating the one or more specimen carriers to about 72° C. and maintaining at about 72° C. while adding amplification reagents;

(g) adding amplification reagents to the one or more specimen carriers;

(h) initiating amplification thermal cycling after addition of amplification reagents, adjusting temperature to about 72° C. and maintaining at about 72° C. for about 2 minutes;

(i) heating the one or more specimen carriers to about 95° C. and maintaining at about 95° C. for about 20 seconds;

(j) repeating steps (h) and (i) about 24 times;

(k) cooling the one or more specimen carriers to about 72° C. and maintaining at about 72° C. for about 10 minutes; and (l) washing fluids through each specimen carrier to remove unwanted materials and incubating at an incubation temperature.

* * * * *